United States Patent [19]

Bailey

[11] Patent Number: 4,510,158

[45] Date of Patent: Apr. 9, 1985

[54] 2-PHENYLINDOLE DERIVATIVES, THEIR USE AS COMPLEMENT INHIBITORS

[75] Inventor: Denis M. Bailey, East Greenbush, N.Y.

[73] Assignee: Sterling Drug Inc., New York, N.Y.

[21] Appl. No.: 586,377

[22] Filed: Mar. 5, 1984

[51] Int. Cl.³ .................... C07D 209/18; A61K 31/40
[52] U.S. Cl. ..................................... 514/415; 548/510; 548/511
[58] Field of Search ................. 548/510, 511; 424/274

[56] References Cited

U.S. PATENT DOCUMENTS 3,551,451 12/1970 Szmuszkovicz ..................... 548/511

FOREIGN PATENT DOCUMENTS 501482 4/1954 Canada ............................... 548/511
3071066 6/1978 Japan ................................... 548/511

OTHER PUBLICATIONS

Patrick, R. A. & Johnson, R. E., Annual Reports in Medicinal Chemistry, vol. 15, Academic Press, New York, NY, 1980; Chapter 20, pp. 193–201.

Freter, K., J. Org. Chem., vol. 40, 2525–2529 (1975).

Primary Examiner—Donald G. Daus
Assistant Examiner—G. Hendricks
Attorney, Agent, or Firm—Thomas L. Johnson; B. Woodrow Wyatt; Paul E. Dupont

[57] ABSTRACT 4-(1-R'-2-phenyl-1H-indol-3-yl)-3-cyclohexene-1-carboxylic acids, 4-(1'R'-2-phenyl-1H-indol-3-yl)cyclohexane-1-carboxylic acids, 4-(1-R'-2-phenyl-1H-indol-3-yl)benzoic acids, the corresponding cyclohexene- and cyclohexane-1,1-dicarboxylic acids, and lower-alkyl esters thereof, wherein R' is hydrogen or lower-alkyl, are prepared by reacting a 1-R'-2-phenyl-1H-indole with a cyclohexanone-4-carboxylic acid or -4,4-dicarboxylic acid, followed as desired by a hydrogenation or aromatization process. The compounds which are free carboxylic acids or salts thereof are useful as complement inhibitors. The corresponding esters are useful as intermediates.

20 Claims, No Drawings

2-PHENYLINDOLE DERIVATIVES, THEIR USE AS COMPLEMENT INHIBITORS

BACKGROUND OF THE INVENTION (a) Field of the Invention

The invention relates to novel 2-phenylindoles having in the 3-position a six-membered carbocyclic group substituted in the 4-position by one or two carboxyl groups, to the preparation thereof, and to the use of the compounds as complement inhibitors.

The term "complement" refers to a complex group of proteins in body fluids that, working together with antibodies and other factors, play an important role as mediators of immune allergic, immunochemical and/or immunopathological reactions. The complement system is essential to combatting the effects of invasion by foreign biological and chemical entities. On the other hand, in the presence of antibody-antigen complexes, the complement proteins are involved in a series of reactions which may lead to irreversible membrane damage in the host organism. Accordingly, substances which are complement inhibitors have been found to be useful in treatment of acute inflammatory events in diseases such as rheumatoid arthritis, lupus erythematosus and glomerulo-nephritis, as documented in *Inflammation: Mechanisms and Control* (Lepow, I. H.; Ward, P. A., Editors), Academic Press, New York, NY, 1972, p. 223; and *Immunological Diseases*, Vol. II (Tolmage, D. W.; Rose, B.; Vaughan, J. H.; Editors), Little, Brown & Co., Boston, 1965, p. 995.

(b) Information Disclosure Statement

A wide variety of chemical substances has been found to cause inhibition at one or more sites of action in the complement pathway; Patrick, R. A. & Johnson, R. E. in *Annual Reports in Medicinal Chemistry*, Vol. 15, Academic Press, New York, NY, 1980; Chapter 20, pp. 193–201. None of the compounds thus far reported to have this activity has a structure closely related to the compounds of the present invention.

Freter, K., J. Org. Chem., Vol. 40, 2525–29 (1975) discloses a series of 3-cycloalkenylindoles prepared by reacting an indole derivative unsubstituted in the 3-position with cyclohexanone or a substituted cyclohexanone. Two of the compounds disclosed are

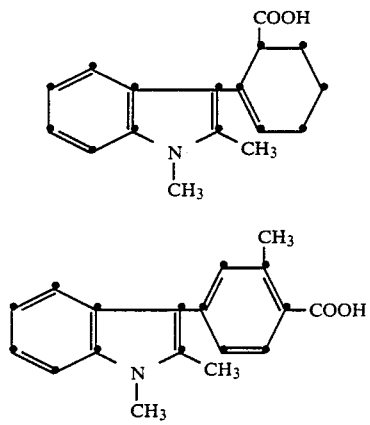

None of the compounds described by Freter has any disclosed utility.

SUMMARY OF THE INVENTION

In a product aspect, the invention relates to compounds of the formula

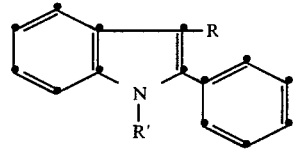

I wherein:
R is selected from the group consisting of:

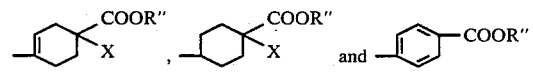

wherein R″ is hydrogen or lower-alkyl and X is hydrogen or —COOR‴, R‴ being hydrogen or lower-alkyl; and R′ is hydrogen or lower-alkyl, including alkali metal salts thereof.

In a further product aspect the invention relates to compositions for inhibiting the mammalian complement system which comprise a complement inhibiting amount of a compound of Formula I where R″ is hydrogen in admixture with one or more pharmaceutically acceptable excipients or diluents.

In a process aspect the invention relates to a process for preparing a compound of Formula I which comprises reacting a 1-R′-2-phenyl-1H-indole with a compound of the formula

in the presence of a strong acid to give a compound of Formula I wherein R is

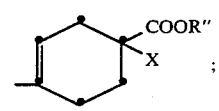

if desired:
hydrogenating a compound of Formula I where R is

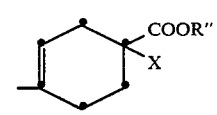

to give a compound of Formula I where R is

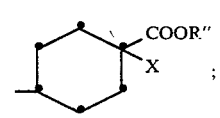

and, if desired:

aromatizing a compound of Formula I where R is

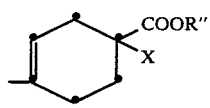

and X is hydrogen to give a compound of Formula I where R is

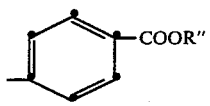

In a further process aspect the invention relates to a method of inhibiting the complement system in a mammal which comprises administering to said mammal an effective complement inhibiting amount of a compound of Formula I where R" is hydrogen.

DETAILED DESCRIPTION INCLUSIVE OF PREFERRED EMBODIMENTS

In the compounds of Formula I, the term "loweralkyl" used in defining the variables, R', R" and R"', stands for alkyl groups having from one to four carbon atoms. The alkali metal salt forms of the compounds include any of the common alkali metals, lithium, sodium or potassium, the last two being preferred.

The compounds of Formula I may be divided into three subgroups as follows:

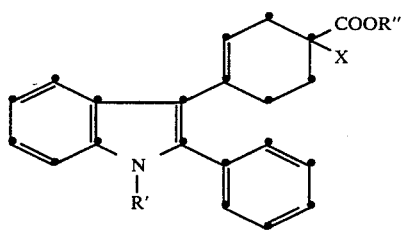

II

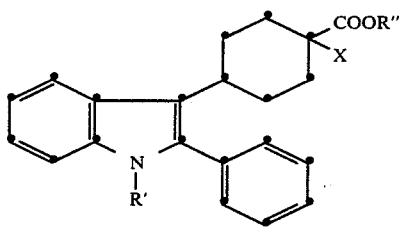

III

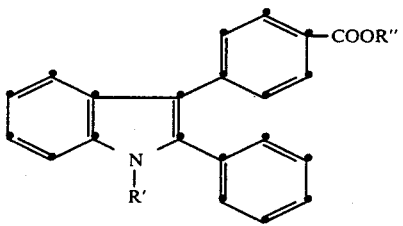

IV wherein R', R" and X have the meanings given above.

In the preparation of the compounds of the invention, the pivotal reaction is the reaction of a 1-R'-2-phenyl-1H-indole with a cyclohexanone derivative of the formula

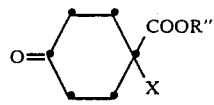

to give a compound of Formula II. The reaction takes place in the presence of a strong acid at ambient temperature or with moderate heating (up to 100° C.). A preferred medium consists of acetic acid, acetic anhydride and phosphoric acid.

The compounds of Formula III are prepared by catalytic hydrogenation of the compounds of Formula II. Nickel, palladium or platinum catalysts can be used, with palladium-on-carbon being a preferred catalyst.

The compounds of Formula IV are prepared by aromatization of the compounds of Formula II using a reagent effective to cause dehydrogenation of the cyclohexene ring. Exemplary of such reagents are benzoquinones such as chloranil and 2,3-dichloro-5,6-dicyanobenzoquinone, diphenylpicrylhydrazyl, N-lithioethylenediamine, palladium, selenium and trityl perchlorate. A preferred procedure involves the use of 2,3-dichloro-5,6-dicyanobenzoquinone in an inert reaction medium at temperatures between about 50° and 150° C.

As desired, the compounds of Formulas II, III or IV, where R' is hydrogen can be converted to the corresponding compounds where R' is lower-alkyl by reaction with a lower-alkyl halide in the presence of a strong base. Also, as desired, the compounds of Formulas II, III or IV, where R" and/or R"' are hydrogen can be conventional esterification procedures be converted to the corresponding compounds where R" and R"' are lower-alkyl, as by reacting the free acid with a lower-alkanol in the presence of a strong acid, or by reacting an alkali metal salt of the acid with a lower-alkyl halide. Conversely, the esters, where R" and/or R"' are lower-alkyl, can be converted to the corresponding free acids by conventional alkaline hydrolysis procedures.

The compounds of Formulas II and III wherein the groups COOR" and X are different may be produced as a mixture of cis and trans forms. If desired, the mixture can be separated by fractional crystallization or chromatographic procedures to give the pure cis and trans isomers.

The following examples will further illustrate the invention.

EXAMPLE 1

4-(2-Phenyl-1H-indol-3-yl)-3-cyclohexene-1-carboxylic acid [II; R', R" and X=H].

A mixture of 100 g (0.52 mol) of 2-phenylindole, 80.8 g (0.57 mol) of 4-cyclohexanonecarboxylic acid, 518 mL of acetic acid, 103.6 mL of acetic anhydride and 25.9 mL of 85% phosphoric acid was stirred at room temperature for 3 days and then chilled in an ice bath to 20° C. The precipitate that resulted was collected, washed with water, pressed dry, taken up in ether, and this solution was washed with water three times and with brine one time, dried over magnesium sulfate, charcoaled, evaporated at 200 mL, and let stand for 2 days to give a precipitate. This precipitate was collected and combined with a second crop to give 72.7 g (44%) of 4-(2-phenyl-1H-indol-3-yl)-3-cyclohexene-1-carboxylic acid, m.p. 178°-179° C. A small portion was recrystallized from acetonitrile, m.p. 180°-183° C.

EXAMPLE 2

4-(2-Phenyl-1H-indol-3-yl)-3-cyclohexene-1,1-dicarboxylic acid [II; R' and R"=H, X=COOH].

Using the method of Example 1, 105.9 g (0.57 mol) of 4,4-cyclohexanonedicarboxylic acid was caused to react with 2-phenylindole and the crude product was slurried with 250 mL of boiling acetonitrile, and collected to give 78 g (42%) of 4-(2-phenyl-1H-indol-3-yl)-3-cyclohexene-1,1-dicarboxylic acid, m.p. 216° C.(dec.). A small portion was recrystallized from ether:chloroform:hexane, m.p. 207°–209° C.

The monosodium salt of 4-(2-phenyl-1H-indol-3-yl)-3-cyclohexene-1,1-dicarboxylic acid was obtained in the form of a colorless powder, m.p. above 340° C.

EXAMPLE 3

4-(1-Methyl-2-phenyl-1H-indol-3-yl)-3-cyclohexene-1,1-dicarboxylic acid [II; R'=CH$_3$, R"=H, X=COOH].

A mixture of 9.0 g (0.043 mol) of 1-methyl-2-phenylindole, 9.3 g (0.05 mol) 4,4-cyclohexanonedicarboxylic acid, 100 mL of acetic acid, 4.7 mL of acetic anhydride, and 1 mL of 85% phosphoric acid was stirred at room temperature for 17 h, and then 100 mL of water was added dropwise to give a white solid which was collected and washed with water. The solid was taken up in ether, washed with water three times and with brine two times, dried over magnesium sulfate, concentrated in vacuo, and crystallized from acetonitrile to give 8.4 g (52%) of 4-(1methyl-2-phenyl-1H-indol-3-yl)-3-cyclohexene-1,1-dicarboxylic acid, m.p. 210°–211° C.

EXAMPLE 4

Methyl 4-(2-phenyl-1H-indol-3-yl)-3-cyclohexene-1-carboxylate [II; R' and X=H, R"=CH$_3$].

A solution of 70.0 g (0.22 mol) of 4-(2-phenyl-1H-indol-3-yl)-3-cyclohexene-1-carboxylic acid (Example 1), 35.2 g (1.1 mol) of methanol, 350 mL of methylene dichloride, and 0.5 mL of methanesulfonic acid was heated under reflux for 21 h. The reaction mixture was cooled, washed with water, dried over sodium sulfate, concentrated in vacuo, and crystallized from ethyl acetate:hexane to give 51.8 g (71%) of methyl 4-(2-phenyl-1H-indol-3-yl)-3-cyclohexene-1-carboxylate in two crops: m.p. 175°–177° C.

Alternatively, the same compound (m.p. 166°–175° C.) was prepared in 81% yield from 31 g (0.098 mol) of acid of Example 1, 47 g (0.34 mol) of powdered potassium carbonate, 47 mL (0.75 mol) of methyl iodide and 117 mL of dimethylformamide using the method described for the preparation of dimethyl 4-(2-phenyl-1H-indol-3-yl)-3-cyclohexene-1,1-dicarboxylate (Example 9 below).

EXAMPLE 5

Methyl 4-(1-methyl-2-phenyl-1H-indol-3-yl)-3-cyclohexene-1-carboxylate [II; R' and R"=CH$_3$, X=H].

A partial solution of 8.06 g (0.122 mol) of crushed potassium hydroxide pellets in 100 mL dimethyl sulfoxide was prepared by stirring the mixture for 45 min. Methyl 4-(2-phenyl-1H-indol-3-yl)-3-cyclohexene-1-carboxylate (Example 4) (12.0 g, 0.036 mol), was added in portions with stirring during 15 min to the partial solution. The resulting dark-red solution was stirred for 45 min, cooled in an ice bath, and treated dropwise with 10.2 g (0.072 mol) of methyl iodide in 50 mL dimethyl sulfoxide. Stirring was continued at room temperature for 3 h. The reaction mixture was cooled again in an ice bath and 250 mL of water was added followed by ether. The ether layer was separated and the aqueous layer was extracted with ether two times. The combined ether solutions were washed with water and brine, dried over magnesium sulfate, concentrated and crystallized from ether:hexane to give 10.4 g of a solid (m.p. 122°–125° C.). This solid was dissolved in chloroform and the solution was charcoaled, concentrated in vacuo, and crystallized from chloroform:ether:hexane two times to give 4.67 g (38%) of methyl 4-(1-methyl-2-phenyl-1H-indol-3-yl)-3-cyclohexene-1-carboxylate, m.p. 135°–136° C.

EXAMPLE 6

4-(1-Methyl-2-phenyl-1H-indol-3-yl)-3-cyclohexene-1-carboxylic acid [II; R'=CH$_3$, R" and X=H].

To a solution of 5.6 g (0.085 mol) of potassium hydroxide in 150 mL of ethanol was added 6.9 g (0.020 mol) of methyl 4-(1-methyl-2-phenyl-1H-indol-3-yl)-3-cyclohexene-1-carboxylate (Example 5). This mixture was heated under reflux until solution resulted. Heating was continued 4 h, then the solution was cooled, concentrated in vacuo, dissolved in water, and made acidic with 2N hydrochloric acid to give a precipitate. The solid was collected, washed with water, dissolved in ether, washed with water, dried over sodium sulfate, charcoaled, concentrated in vacuo, and recrystallized twice from ether:hexane to give 5.6 g (85%) of 4-(1-methyl-2-phenyl-1H-indol-3-yl)-3-cyclohexene-1-carboxylic acid, m.p. 171°–172° C.

EXAMPLE 7

4-(1-Ethyl-2-phenyl-1H-indol-3-yl)-3-cyclohexene-1-carboxylic acid [II; R'=C$_2$H$_5$, R" and X=H].

To 40 g (0.85 mol) of sodium hydride (50% in oil) that was washed with pentane three times and stirred in 60 mL of dimethylformamide was added 12.2 g (0.38 mol) of 4-(2-phenyl-1H-indol-3-yl)-3-cyclohexene-1-carboxylic acid (Example 1) in portions. After the addition was complete, the mixture was heated at 50° C. for 2 h, then cooled in an ice bath, and 8 mL (0.10 mol) of ethyl iodide was added dropwise. The mixture was stirred at room temperature overnight and at 40° C. for 3 h. The reaction mixture was cooled, quenched with 250 mL of cold water, and extracted with 500 mL of ether. The ether extract was washed with water two times and brine one time, dried over magnesium sulfate, charcoaled, and concentrated in vacuo to give 13.5 g of an oil. This oil comprising the ethyl ester of the desired product was combined with a solution of 2.6 g (0.04 mol) of potassium hydroxide in 160 mL of ethanol and stirred at room temperature overnight. The reaction mixture was poured into 400 mL of cold water, and the resulting mixture was washed with methylene dichloride three times and ether one time, filtered through filter cell, and made acidic with acetic acid to give a precipitate. This precipitate was collected, washed with water, and dried at 85° C. (0.1 mm) overnight to give 10.7 g (80%) of 4-(1-ethyl-2-phenyl-1H-indol-3-yl)-3-cyclohexene-1-carboxylic acid, m.p. 147°–150° C.

EXAMPLE 8

4-(2-Phenyl-1-propyl-1H-indol-3-yl)-3-cyclohexene-1-carboxylic acid [II; R'=(CH$_2$)$_2$CH$_3$, R" and X=H].

Using the method described in Example 7, 15.0 g (0.047 mol) of 4-(2-phenyl-1H-indol-3-yl)-3-cyclohexene-1-carboxylic acid (Example 1) was alkylated with n-propyl bromide to give 8.9 g (53%) of the title compound, m.p. 126°-127° C.

EXAMPLE 9

4-(1-Ethyl-2-phenyl-1H-indol-3-yl)-3-cyclohexene-1,1-dicarboxylic acid [II; R'=C$_2$H$_5$, R"=H, X=COOH].

A mixture of 56 g (0.15 mol) of 4-(2-phenyl-1H-indol-3-yl)-3-cyclohexene-1,1-dicarboxylic acid (Example 2), 136 g (0.99 mol) of powdered potassium carbonate, and 369 mL of dimethylformamide was stirred at room temperature 2 h. Methyl iodide (146.8 mL, 2.08 mol), was added and the mixture was heated under reflux in a hot water bath for 4 h. After stirring overnight at room temperature, the excess methyl iodide was removed by concentrating the reaction mixture in vacuo at 30° C. The mixture was then poured into 1200 mL water and extracted with ethyl acetate three times. The combined ethyl acetate extracts were washed with water two times and brine one time, dried over magnesium sulfate, and concentrated in vacuo to give 63.1 g of the crude dimethyl ester that was used in subsequent reactions without further purification.

To 1.8 g (0.37 mol) of sodium hydride (50% in oil) that was washed three times with pentane and slurried and stirred in 50 mL of dimethylformamide was added 12 g (0.031 mol) of the crude dimethyl ester in portions. After addition was complete, the mixture was heated at 50° C. for 2 h then cooled in an ice bath, and 3.0 mL (0.048 mol) of ethyl iodide was added dropwise. The mixture was stirred at room temperature overnight and at 40° C. for 3 h. The reaction mixture was cooled, quenched with 300 mL of cold water, and extracted with ether. The ether extract was washed with water two times and brine one time, dried over magnesium sulfate, and concentrated in vacuo to give 11.8 g of an oil comprising the dimethyl ester of the desired product which was combined with 4.3 g (0.065 mol) of potassium hydroxide, 11.8 mL of water and 217 mL of ethanol, and heated under reflux for 5 h. The precipitate was collected (7.1 g), taken up in water, filtered, and made acidic with 10% hydrochloric acid to give a precipitate. This precipitate was collected, washed with water, and dried at 70° C. (0.1 mm) overnight to give 5.7 g (49%) of 4-(1-ethyl-2-phenyl-1H-indol-3-yl)-3-cyclohexene-1,1-dicarboxylic acid, m.p. 160°-165° C.

Samples of the intermediate esters were purified to give the following compounds:

Dimethyl 4-(2-phenyl-1H-indol-3-yl)-3-cyclohexene-1,1-dicarboxylate [II; R'=H, R"=CH$_3$, X=COOCH$_3$], m.p. 111°-112° C. (from ether).

Dimethyl 4-(1-ethyl-2-phenyl-1H-indol-3-yl)-3-cyclohexene-1,1-dicarboxylate [II; R'=C$_2$H$_5$, R"=CH$_3$, X=COOCH$_3$], yellow crystals from acetonitrile, m.p. 91°-98° C.

EXAMPLE 10

4-(2-Phenyl-1-propyl-1H-indol-3-yl)-3-cyclohexene-1,1-dicarboxylic acid [II; R'=(CH$_2$)$_2$CH$_3$, R"=H, X=COOH] was prepared by the procedure of Example 9, except that the ethyl iodide of that example was replaced by a molar equivalent amount of n-propyl bromide, and was obtained in the form of its dipotassium salt monohydrate, m.p. 325° C.

The intermediate ester, dimethyl 4-(2-phenyl-1-propyl-1H-indol-3-yl)-3-cyclohexene-1,1-dicarboxylate [II; R'=(CH$_2$)$_2$CH$_3$, R"=CH$_3$, X=COOCH$_3$] was obtained pure in the form of a colorless solid, m.p. 86°-89° C. when recrystallized from ether-pentane.

EXAMPLE 11

4-(2-Phenyl-1H-indol-3-yl)cyclohexane-1,1-dicarboxylic acid [III; R' and R"=H, X=COOH].

A solution of 5.3 g (0.015 mol) of 4-(2-phenyl-1H-indol-3-yl)-3-cyclohexene-1,1-dicarboxylic acid (Example 2) in 100 mL of ethanol was combined with 1.2 g of 10% palladium-on-carbon catalyst and hydrogenated on a Parr apparatus at room temperature for 3 h. After the catalyst was removed, the solution was concentrated in vacuo to a gum. This gum was crystallized from ether:hexane and then recrystallized three times from ether:hexane to give 4.0 g (74%) of 4-(2-phenyl-1H-indol-3-yl)cyclohexane-1,1-dicarboxylic acid, m.p. 196°-197° C.

EXAMPLE 12

4-(1-Methyl-2-phenyl-1H-indol-3-yl)cyclohexane-1,1-dicarboxylic acid [III; R'=CH$_3$, R"=H, X=COOH].

Using the method of Example 11, except that dioxane replaced ethanol as solvent and product was recrystallized from acetone:hexane one time, 7.5 g (0.020 mol) of 4-(1-methyl-2-phenyl-1H-indol-3-yl)-3-cyclohexene-1,1-dicarboxylic acid (Example 3) was hydrogenated to give 3.8 g (51%) of 4-(1-methyl-2-phenyl-1H-indol-3-yl)cyclohexane-1,1-dicarboxylic acid, m.p. 230° C.(decompn.).

EXAMPLE 13

(cis)-4-(1-Methyl-2-phenyl-1H-indol-3-yl)cyclohexane-1-carboxylic acid and (trans)-4-(1-Methyl-2-phenyl-1H-indol-3-yl)-cyclohexane-1-carboxylic acid [III; R'=CH$_3$, R" and X=H].

Using the method of Example 11, 35 g (0.10 mol) of methyl 4-(1-methyl-2-phenyl-1H-indol-3-yl)-3-cyclohexene-1-carboxylate (Example 5) was hydrogenated to give 35 g of a gum that was a mixture of two products (SiO$_2$ TLC, toluene eluate, RFs: 0.3 and 0.4). The gum was triturated with ether and the solid that formed was collected, washed with ether, and dried to give 18.8 g of solid that was recrystallized from heptane to give 14.4 g (41%) of methyl (cis)-4-(1-methyl-2-phenyl-1H-indol-3-yl)cyclohexane-1-carboxylate [III; R' and R"=CH$_3$, X=H] with TLC RF=0.4, m.p. 125°-126° C.; $^{13}$C NMR (CDCl$_3$) δ175.6 (COO), 137.2, 136.6, 132.4, 130.7, 128.1, 127.8, 126.2, 121.2, 120.3, 118.7, 118.1, 109.2 (indole and phenyl), 51.3 (CH$_3$O), 38.3 (CHCOO), 35.8 (indole-CH), 30.4 (CH$_3$N), 29.1 (C$_2$ and C$_6$), 27.8 (C$_3$ and C$_5$).

The ether filtrate was concentrated to a gum (16 g). This gum was dissolved in a minimum of toluene and subjected to HPLC chromatography on silica using toluene:hexane (9:1) as eluate to give a pure fraction as determined by TLC of the RF=0.3 compound which was recrystallized from heptane to give 0.8 g of methyl (trans)-4-(1-methyl-2-phenyl-1H-indol-3-yl)cyclohexane-1-carboxylate [III; R' and R"=CH$_3$, X=H], m.p. 141°-142° C.; $^{13}$C NMR (CDCl$_3$) δ176.4 (COO), 137.2, 137.0, 132.3, 130.6 128.1, 127.9, 126.1, 121.2, 120.1, 118.6, 117.4, 109.4 (indole and phenyl), 51.3 (CH$_3$O), 42.9 (CHCOO), 35.7 (indole-CH), 32.2 (C$_2$ and C$_6$), 30.4 (CH$_3\overline{\text{N}}$), 29.4 (C$_3$ and C$_5$).

Using the method of Example 6, except that the product was recrystallized from aqueous dioxane, 7 g (0.02 mol) of cis-methyl ester was hydrolyzed into 5.1 g (77%) of (cis)-4-(1-methyl-2-phenyl-1H-indol-3-yl)cyclohexane-1-carboxylic acid, m.p. 270°–271° C., $^{13}$C NMR (DMSO-d$_6$) δ175.7 (COO), 136.9, 136.2, 131.6, 130.2, 128.0, 127.8, 125.7, 120.7, 119.4, 118.1, 117.3, 109.6 (indole and phenyl), 37.5 (CHCOO), 35.3 (indole-CH), 30.1 (CH$_3$N), 28.6 (C$_2$ and C$_6$), 27.3 (C$_3$ and C$_5$).

Similarly, 5.0 g (0.014 mol) of trans methyl ester was transformed into 2.8 g (60%) of (trans)-4-(1-methyl-2-phenyl-1H-indol-3-yl)cyclohexane-1-carboxylic acid, m.p. 178°–180° C. (from ether); $^{13}$C NMR (DMSO-d$_6$) δ176.2 (COO), 136.8, 136.4, 131.7, 130.2, 128.0, 127.8, 125.7, 120.7, 119.6, 118.2, 116.7, 109.5 (indole and phenyl), 42.0 (CHCOO), 35.4 (indole-CH), 31.6 (C$_2$ and C$_6$), 30.0 (CH$_3$—N), 29.1 (C$_3$ and C$_5$).

EXAMPLE 14

(cis)-4-(1-Methyl-2-phenyl-1H-indol-3-yl)-1,1-cyclohexane-dicarboxylic acid monomethyl ester [III; R′=CH$_3$, R″=H, X=COOCH$_3$].

To 1.8 g (0.037 mol) of sodium hydride (50% in oil) that was washed with pentane three times and stirred in 50 mL of dimethylformamide was added dropwise 11.8 g (0.030 mol) of crude dimethyl 4-(2-phenyl-1H-indol-3-yl)-3-cyclohexene-1,1-dicarboxylate (Example 9) in 30 mL of dimethylformamide. After the addition was complete, the mixture was heated at 50° C. for 2 h, then cooled in an ice bath, and 3.0 mL (0.048 mol) of methyl iodide was added dropwise. The mixture was stirred at room temperature overnight and at 50° C. for 3 h. The reaction mixture was poured into 300 mL of water and extracted with ether two times. The combined ether extracts were washed with water two times and brine one time, dried over magnesium sulfate, and concentrated in vacuo to give 10.6 g of resinous residue.

Using the method of Example 11, except that the product was crystallized from ethanol, 10 g (0.025 mol) of the above resinous residue was hydrogenated to give 5.0 g (44% overall) of dimethyl 4-(1-methyl-2-phenyl-1H-indol-3-yl)-1,1-cyclohexane dicarboxylate [III; R′ and R″=CH$_3$, X=COOCH$_3$], m.p. 134°–135° C.

To a solution of 3.2 g (0.049 mol) of potassium hydroxide in 50 mL of methanol and 5 drops of water was added 2.0 g (0.0049 mol) of above-described dimethyl ester. This solution was heated under reflux for 1 h and then concentrated in vacuo at room temperature. The residue was suspended in water, made acidic with 3N hydrochloric acid, and extracted with ether. The ether extract was washed with brine two times, dried over magnesium sulfate, concentrated in vacuo, and crystallized from ether:hexane to give 0.8 g (42%) of (cis)-4-(1-methyl-2-phenyl-1H-indol-3-yl)-1,1-cyclohexanedicarboxylic acid monomethyl ester, m.p. 192°–193° C.

EXAMPLE 15

4-(2-Phenyl-1H-indol-3-yl)benzoic acid [IV; R′ and R″=H].

To a solution of 43.4 g (0.13 mol) of methyl 4-(2-phenyl-1H-indol-3-yl)-3-cyclohexene-1-carboxylate (Example 4) in 400 mL of dioxane was added 63.6 g (0.28 mol) of 2,3-dichloro-5,6-dicyanobenzoquinone followed by 50 mL of dioxane. The resulting pea-green suspension was stirred and heated under reflux for 19 h. The reaction mixture was cooled in an ice bath and the insoluble 2,3-dichloro-5,6-dicyanohydroquinone was collected, washed with hot dioxane:hexane, and dried [51.3 g (80%), m.p. 302°–305° C.]. The reaction mixture filtrate was concentrated and partitioned between ethyl acetate:toluene and ice water. The organic layer was separated, dried over sodium sulfate, and concentrated in vacuo to give 40 g of a semi-solid. This semi-solid was subjected to column chromatography on 1000 g of silica using toluene and toluene:ethyl acetate (9:1) as eluting solvents, and gave 27.0 g of a red-orange solid, m.p. 163°–165° C. Purification of this material by HPLC on silica using hexane:toluene (1:4) as eluting solvent, followed by crystallization from ethyl acetate:hexane gave 25.2 g (59%) of methyl 4-(2-phenyl-1H-indol-B 3-yl)benzoate [IV; R′=H, R″=CH$_3$].

A mixture of 13.2 g (0.040 mol) of the methyl ester and 11.2 g (0.17 mol) of potassium hydroxide in 250 mL of ethanol was stirred and heated under gentle reflux for 4 h to give a solution. The cooled solution was concentrated in vacuo, partitioned between cold water and ether, and the aqueous layer was separated, made acidic with 6N hydrochloric acid, and extracted with ethyl acetate. The ethyl acetate extract was dried over sodium sulfate, concentrated in vacuo, and triturated with hexane to give a solid which was collected and recrystallized three times from acetone:ethyl acetate:hexane to give 8.9 g (71%) of 4-(2-phenyl-1H-indol-3-yl)benzoic acid, m.p. 252°–253° C.

EXAMPLE 16

By a procedure analogous to that of Example 15, 10.2 g of methyl 4-(1-methyl-2-phenyl-1H-indol-3-yl)-3-cyclohexene-1-carboxylate (Example 5) was aromatized to methyl 4-(1-methyl-2-phenyl-1H-indol-3-yl)benzoate [IV; R′ and R″=CH$_3$], m.p. 165°–166° C., and the latter hydrolyzed to yield 7.3 g (74%) of 4-(1-methyl-2-phenyl-1H-indol-3-yl)-benzoic acid [IV; R′=CH$_3$, R″=H], m.p. 235°–240° C. (from aqueous dioxane).

The compounds of Formula I wherein at least one free carboxyl group is present demonstrate complement inhibitory activity in vitro and/or in vivo. The corresponding lower-alkyl esters are not active but are useful as intermediates in preparing the free acids, as illustrated above.

The compounds were evaluated in vitro for their inhibition of human complement (C1–C9) using hemolytic molecular titrations, and the reverse passive Arthus reaction (RPAR) in guinea pigs was chosen as a complement mediated model of acute inflammation to be used to identify compounds with in vivo complement inhibitory activity.

Hemolytic molecular titrations of classical complement activity were performed according to Rapp and Borsos [*Molecular Basis of Complement Action*, Appleton-Century-Crofts, New York, NY, 1970] and complement inhibition assessed according to Hong et al. (*J. Immunol.* 1979, Vol. 122, 2418). Operationally, the test compound was maintained in the presence of complement during the lytic reaction of sensitized erythrocytes. Equal volumes (0.2 ml) of normal human serum (NHS), diluted in GVB++ [Mayer, M. M. in *Kabat and Mayer's Experimental Immunochemistry*, 2nd Ed.; Charles C. Thomas, Springfield, Ill., 1961, p. 133] to effect lysis of Z=1, and test compound at various concentrations were mixed at 0° C. The dilution of NHS effecting 63% lysis of optimally sensitized sheep erythrocytes (EA) was previously determined (1:100 to 1:200). EA (0.2 ml of 1.5×10$^8$ cells/ml) and 1.8 ml of GVB++ were added to the reaction mixture followed by incubating at 37° C. for 60 min. The extent of lysis was determined spectrophotometrically at 412 nm. The ratio of treated to untreated (Z/Zo) reaction mixtures was determined as a function of test compound concentration. The concentration of test compound effecting 50% suppression (Z/Zo=0.5 or IC$_{50}$) was determined.

Reverse Passive Arthus Reaction (RPAR): Male guinea pigs (250–300 g) were administered chicken egg albumin (CEA) intravenously (20 mg/kg) immediately before intradermal injection of 0.2 ml goat anti-CEA containing 2.4 mg Ab protein/ml. The hemorrhagic response was allowed to develop for 4 h and the animals sacrificed and skin lesions excised. The skin sections were homogenized, water extracted, cleared, and the optical density at 541 or 412 nm determined. A paired Student t test was used to estimate significant inhibition of groups treated with the test compound. P values less than 0.025 were considered significant. The test compound was administered i.p. 2 h before eliciting the Arthus response and i.v. administration was effected 20 min before elicitation.

The following Table lists the results obtained from the testing of the compounds of the invention. Gold sodium thiomalate, a known complement inhibitor, and cobra venom factor, known to suppress the RPAR by depleting complement levels, were tested as reference materials and are included in the Table.

| Example | Classical Complement Pathway Inhibition IC$_{50}$ (μM) | RPAR % Inhib. | Dose (mg/kg) |
|---|---|---|---|
| 1 | 135 ± 2 | 64 ± 7$^a$ | 80 iv |
| 2 | 485 ± 17 | 38 ± 8$^b$ | 100 ip |
| 3 | 149 ± 25 | NT$^d$ | |
| 6 | 34 ± 3 | 78 ± 6$^b$ | 300 ip |
| 7 | 65 ± 5 | NT | |
| 8 | 93 ± 44 | NT | |
| 9 | 130 ± 20 | NT | |
| 11 | 425 ± 105 | NT | |
| 12 | 231 ± 7 | NT | |
| 13 (cis-isomer) | >1000 | 66 ± 5$^b$ | 100 ip |
| 13 (trans-isomer) | 42 ± 21 | 55 ± 8$^a$ | 100 ip |
| 14 | 51 ± 15 | 76 ± 5$^a$ | 100 ip |
| 15 | 105 ± 4 | NT | |
| 16 | 51 ± 11 | 44 ± 14$^c$ | 100 ip |
| Gold Sodium Thiomalate | 1070 ± 90 | | |
| Cobra Venom Factor | | ED$_{50}$ = 7.9 units/kg ip | |

$^a$p = 0.001
$^b$p = 0.01
$^c$p = 0.025
$^d$not tested

The compounds tested in the RPAR test were active by the intravenous (iv) or intraperitoneal (ip) route but not by the oral route. Although the cis-isomer of the compound of Example 13 was not active in vitro at the highest dose tested, it was active in the RPAR test. A possible explanation for this apparent anomaly is that the cis-isomer in vivo is metabolized to an active complement inhibitor, or that it acts by a different complement independent mechanism.

The compounds of the invention which are active as complement inhibitors can be prepared for use by conventional pharmaceutical procedures: that is, by dissolving or suspending them in a pharmaceutically acceptable vehicle, e.g. water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g. calcium carbonate, starch, lactose, talc, magnesium stearate, gum acacia and the like.

I claim:

1. A compound of the formula:

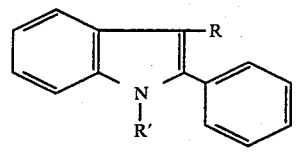

wherein:

R is selected from the group consisting of:

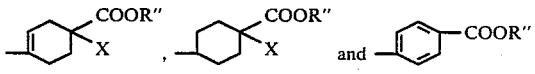

wherein R" is hydrogen or lower-alkyl and X is hydrogen or —COOR'", R'" being hydrogen or lower-alkyl; and R' is hydrogen or lower-alkyl; or an alkali metal salt thereof.

2. A compound according to claim 1 wherein R" is hydrogen.

3. A compound according to claim 2 wherein R is

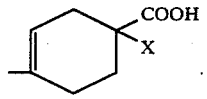

4. 4-(2-Phenyl-1H-indol-3-yl)-3-cyclohexene-1-carboxylic acid, according to claim 3.

5. 4-(2-Phenyl-1H-indol-3-yl)-3-cyclohexene-1,1-dicarboxylic acid, according to claim 3.

6. 4-(1-Methyl-2-phenyl-1H-indol-3-yl)-3-cyclohexene-1-carboxylic acid, according to claim 3.

7. 4-(1-Methyl-2-phenyl-1H-indol-3-yl)-3-cyclohexene-1,1-dicarboxylic acid, according to claim 3.

8. 4-(1-Ethyl-2-phenyl-1H-indol-3-yl)-3-cyclohexene-carboxylic acid, according to claim 3.

9. 4-(2-Phenyl-1-propyl-1H-indol-3-yl)-3-cyclohexene-1-carboxylic acid, according to claim 3.

10. 4-(1-Ethyl-2-phenyl-1H-indol-3-yl)-3-cyclohexene-1,1-dicarboxylic acid, according to claim 3.

11. A compound according to claim 2 wherein R is

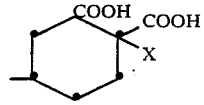

12. 4-(2-Phenyl-1H-indol-3-yl)cyclohexane-1,1-dicarboxylic acid, according to claim 11.

13. (cis)-4-(1-Methyl-2-phenyl-1H-indol-3-yl)cyclohexane-1-carboxylic acid and (trans)-4-(1-methyl-2-phenyl-1H-indol-3-yl)cyclohexane-1-carboxylic acid, according to claim 11.

14. 4-(1-Methyl-2-phenyl-1H-indol-3-yl)cyclohexane-1,1-dicarboxylic acid, according to claim 11.

15. (cis)-4-(1-Methyl-2-phenyl-1H-indol-3-yl)-1,1-cyclohexanedicarboxylic acid monomethyl ester, according to claim 11.

16. A compound according to claim 2 wherein R is

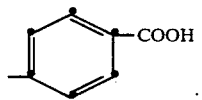

17. 4-(2-Phenyl-1H-indol-3-yl)benzoic acid, according to claim 16.

18. 4-(1-Methyl-2-phenyl-1H-indol-3-yl)benzoic acid, according to claim 16.

19. A composition for inhibiting the mammalian complement system which comprises a complement inhibitory amount of a compound according to claim 2 in admixture with one or more pharmaceutically acceptable excipients or diluents.

20. A method of inhibiting the complement system in a mammal which comprises administering to said mammal an effective complement inhibitory amount of a composition according to claim 19.

* * * * *

UNITED STATES PATENT AND TRADEMARK OFFICE
CERTIFICATE OF CORRECTION

PATENT NO. : 4,510,158
DATED : April 9, 1985
INVENTOR(S) : Denis M. Bailey

It is certified that error appears in the above-identified patent and that said Letters Patent is hereby corrected as shown below:

Column 4, line 33, "can be" should read --can by--; line 63, "at 200 mL" should read --to 200 mL--.

Column 10, line 12, "indol-B 3-" should read --indol-3- --.

Column 12, line 43, Claim 8, "cyclohexene-" should read --cyclohexene-1- --.

Column 12, lines 51-55, Claim 11,

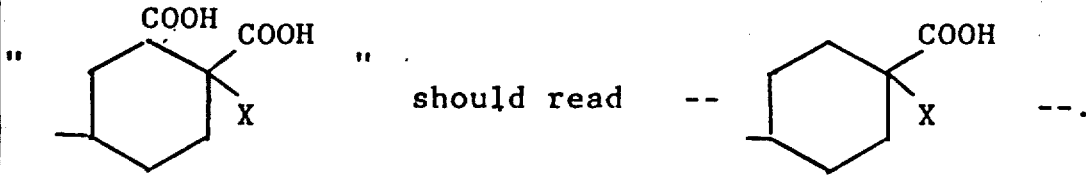

Signed and Sealed this

Third Day of September 1985

[SEAL]

Attest:

DONALD J. QUIGG

Attesting Officer   Acting Commissioner of Patents and Trademarks - Designate